United States Patent [19]

Kovács et al.

[11] Patent Number: 4,565,694
[45] Date of Patent: Jan. 21, 1986

[54] CONTRACEPTIVE VAGINAL TABLETS

[76] Inventors: András Kovács, Bajcsy Zs. ut 19/a, 1065 Budapest; Rudolf Szebeni, Béke u. 48, 2131 Göd; Béla Köszegi, Corvin körut 52, 1192 Budapest, all of Hungary

[21] Appl. No.: 621,905

[22] PCT Filed: Oct. 7, 1983

[86] PCT No.: PCT/HU83/00052
§ 371 Date: Jun. 7, 1984
§ 102(e) Date: Jun. 7, 1984

[87] PCT Pub. No.: WO84/01502
PCT Pub. Date: Apr. 26, 1984

[30] Foreign Application Priority Data

Oct. 7, 1982 [HU] Hungary ............................ 3211/82

[51] Int. Cl.$^4$ ............................................. A61K 31/79
[52] U.S. Cl. ...................................... 424/80; 514/577; 514/682; 514/843
[58] Field of Search ......... 424/80, 331, 303, DIG. 14; 514/577

[56] References Cited

U.S. PATENT DOCUMENTS

| | | | |
|---|---|---|---|
| 3,062,715 | 11/1962 | Reese | 424/44 X |
| 4,031,202 | 6/1977 | Laughlin et al. | 424/28 |
| 4,242,359 | 12/1980 | Cooper et al. | 424/325 |
| 4,323,548 | 4/1982 | Scherm | 424/44 |
| 4,432,967 | 2/1984 | Szymanski | 424/78 |
| 4,439,441 | 3/1984 | Hallesy et al. | 424/273 R |

OTHER PUBLICATIONS

Chemical Abstracts, 76:42280r (1972).
Merck Index, p. 5652 (¶ 5653), 9th ed. 1976.

*Primary Examiner*—Leonard Schenkman
*Attorney, Agent, or Firm*—Stevens, Davis, Miller & Mosher

[57] ABSTRACT

The invention relates to contraceptive vaginal tablets as well as to a process for preparing them. The tablets of the invention have the following composition:
0.2 to 3 parts by weight of boric acid,
10 to 20 parts by weight of tartaric acid,
1 to 2 parts by weight of vitamin $K_3$-sodium bisulfite adduct,
0.8 to 1.2 parts by weight of polyvinyl pyrrolidone,
2 to 5 parts by weight of magnesium stearate,
8 to 12 parts by weight of carboxymethyl cellulose,
8 to 12 parts by weight of lactose and
50 to 65 parts by weight of microcrystalline cellulose.

The vaginal tablets contain preferably 5 to 10 mg of vitamin $K_3$-sodium bisulfite adduct and have a total weight of 500 mg.

The tablets of the invention are prepared preferably in such way that the boric acid, the tartaric acid and the vitamin $K_3$-sodium bisulfite adduct, as well as the polyvinyl pyrrolidone, the magnesium stearate, the carboxymethyl cellulose, the lactose and the microcrystalline cellulose are homogenized separately to powder mixtures thereafter the powder mixtures are mixed and pressed to tablets.

The tablets should be wetted and put into the back-vaginal fornix 10 minutes before the coitus.

2 Claims, No Drawings

CONTRACEPTIVE VAGINAL TABLETS

The invention relates to contraceptive vaginal tablets being free from hormones as well as to a process for preparing them.

Three methods are known—except for operations—which hinder the occurrence of undesirable pregnancy. These methods are the use of condoms, the insertion of intrauterine instruments and the insertion of vaginal pessaries (mechanical instruments) which hinder the occurrence of the pregnancy by using hormonal preparations or local spermicidal preparations free from hormones.

All the known methods have, however, certain disadvantages which do not make possible general application. It is known that not every conceptive age-group may use the preparations containing hormones. However, certain persons, who could take these preparations in view of their age, are deprived of employing them owing to the side effects. From among the mechanical instruments the condom and the vaginal pessary cause in certain cases uncomfortable feeling or require preparation which destroys the illusion. The intrauterine instruments are free from these disadvantages, but have the disadvantage that not all persons may wear them as well as the fact that the youngest age-group may not use them. A further disadvantage of these instruments is that they may be inserted only by the physician. In case of the hormone free preparation no contraindication of the age-group exists. These are rarely applied per se, however since they are not reliable enough.

The efficiency of the known contraceptive instruments and methods is characterized by the so-called Pearl-index. This is a number which shows that from among 100 conceptive women using the instrument or method in question how many will be pregnant during a year. The Pearl-index of the contraceptive instruments and methods is stated in the following Table.

TABLE

| | |
|---|---|
| vaginal irrigation | 29.3–40.8 |
| coitus interrupted | 12–38 |
| Ogino-Knaus rule | 12–34.5 |
| foam tablet | 11.9–42.8 |
| vaginal pellet | 7.7–42.3 |
| diaphragm | 6.1–33.6 |
| jelly | 6.4–41 |
| vaginal pessary | 6.0–29 |
| condom | 6–28 |
| intrauterine instrument | 0.9–8 |
| hormonal preparation | 0–1.7 |

From the data of this Table it can be seen that only the hormonal preparation possess the safety desired, the efficiency of the preparations containing only chemical substances fall far behind that of the hormonal preparations.

The aim of the present invention is to find a vaginal tablet being free from hormones which possess the same efficiency as the hormonal preparations and do not show the disadvantages thereof, which tablets may be used without any limitation of the age or the physical condition of the person using them.

The vitamin $K_3$ and the adduct thereof with sodium bisulfite are widely used in the therapy e.g. for treating icterus occlusion, pre- and postoperative treatment in cholemia, biliary fistula, ulcerative colitis, dysentery, steatorrhea, sprue, celiac disease, hemophilia of the newborn, jaundice, salicylism, purpura, thormbophenia, serum sickness, urticaria, haemoptoe. The contraceptive effect of these compounds has not been described yet.

The therapeutic use of boric acid and tartaric acid is also known. The boric acid is used for rinsing cavities owing to its weak disinfectant effect, the tartaric acid is applied for regulating the pH of the preparations due to its weak acidic reaction.

It was surprisingly found that a preparation, which correspond to the above requirements, may be obtained when 0.2 to 3.0 parts by weight of boric acid.

10.0 to 20 parts by weight of tartaric acid.

1 to 2 parts by weight of vitamin $K_3$-sodium bisulfite adduct, 0.8 to 1.2 parts by weight of polyvinyl pyrrolidone.

2 to 5 parts by weight of magnesium stearate, 8 to 12 parts by weight of carboxymethyl cellulose, 8 to 12 parts by weight of lactose and 50 to 65 parts by weight of microcrystalline cellulose are homogenized and thereafter pressed to tablets.

The tablets contain preferably 5 mg of vitamin $K_3$-sodium bisulfit adduct per tablets. Such a tablet has a total weight of about 500 mg.

The vaginal tablets of the invention should be wetted before insertion and thereafter inserted into the back-vaginal fornix. Here the tablets disintegrate quickly owing to the moisture and form a suspension. This suspension covers the cervix and paralyzes the spermiums being introduced. The rest of the preparation may be removed by irrigation. The use of the tablets does not cause uncomfortable feeling, the tablets disintegrated in the vagina do not have any noxious side effect.

Further details of the invention are shown in the following Examples without any limitation thereto.

EXAMPLE 1

Homogeneous powder mixture is prepared from 2.0 g of powdered boric acid. 100.0 g of powdered tartaric acid and 100.0 g of microcrystalline cellulose. Separately 10.0 g of vitamin $K_3$-sodium bisulfit adduct. 10.0 g of polyvinyl pyrrolidone (Polyplasdon XL). 30.0 g of magnesium stearate and 100.0 g of carboxymethyl cellulose are homogenized. The two powder mixtures are mixed thereafter 648.0 g of microcrystalline cellulose are admixed. 1000.0 g of the powder mixture are obtained, from which 2000 tablets each weighing 500 mg and having a diameter of 12 mm are pressed without edges.

Some properties of the tablets so obtained are summarized as follows:

| abrasion hardness (ERWEKA-TAP): | |
|---|---|
| after 5 minutes | after 10 minutes |
| 1.46% | 3.02% |
| 1.29% | 2.86% |
| compression strength (ERWEKA): | 14.3 N |
| average height of the tablets: | 4.52 mm |
| disintegration time (flask method according to PA.Mg.VI): | 9 to 10 minutes. |

EXAMPLE 2

Tablets are prepared according to the process described in Example 1 with the following composition:

| | |
|---|---|
| boric acid | 5.0 mg |

-continued

| | |
|---|---|
| tartaric acid | 50.0 mg |
| vitamin K$_3$-sodium bisulfite adduct | 5.0 mg |
| polyvinyl pyrrolidone | 5.0 mg |
| magnesium stearate | 15.0 mg |
| carboxymethyl cellulose | 50.0 mg |
| lactose | 50.0 mg |
| microcrystalline cellulose | 320.0 mg |
| | 500.0 mg |

EXAMPLE 3

Tablets are prepared according to the process described in Example 1 with the following composition:

| | |
|---|---|
| boric acid | 15.0 mg |
| tartaric acid | 50.0 mg |
| vatamin K$_3$-sodium bisulfite adduct | 5.0 mg |
| polyvinyl pyrrolidone | 5.0 mg |
| magnesium stearate | 15.0 mg |
| carboxymethyl cellulose | 50.0 mg |
| lactose | 50.0 mg |
| microcrystalline cellulose | 310.0 mg |
| | 500.0 mg |

EXAMPLE 4

Tablets are prepared according to the process described in Example 1 with the following composition:

| | |
|---|---|
| boric acid | 1.0 mg |
| tartaric acid | 100.0 mg |
| vitamin K$_3$-sodium bisulfite adduct | 5.0 mg |
| polyvinyl pyrrolidone | 5.0 mg |
| magnesium stearate | 15.0 mg |
| carboxymethyl cellulose | 50.0 mg |
| lactose | 50.0 mg |
| microcrystalline cellulose | 274.0 mg |
| | 500.0 mg |

EXAMPLE 5

Tablets are prepared with the following composition:

| | |
|---|---|
| boric acid | 1.0 mg |
| tartaric acid | 50.0 mg |
| vitamin K$_3$-sodium bisulfite adduct | 10.0 mg |
| polyvinyl pyrrolidone | 5.0 mg |
| magnesium stearate | 15.0 mg |
| carboxymethyl cellulose | 50.0 mg |
| lactose | 50.0 mg |
| microcrystalline cellulose | 319.0 mg |
| | 500.0 mg |

EXAMPLE 6

Tablets are prepared with the following composition:

| | |
|---|---|
| boric acid | 5.0 mg |
| tartaric acid | 50.0 mg |
| vitamin K$_3$-sodium bisulfite adduct | 10.0 mg |
| polyvinyl pyrrolidone | 5.0 mg |
| magnesium stearate | 15.0 mg |
| carboxymethyl cellulose | 50.0 mg |
| lactose | 50.0 mg |
| microcrystalline cellulose | 315.0 mg |

-continued

| | |
|---|---|
| | 500.0 mg |

EXAMPLE 7

Tablets are prepared with the following composition:

| | |
|---|---|
| boric acid | 15.0 mg |
| tartaric acid | 50.0 mg |
| vitamin K$_3$-sodium bisulfite adduct | 10.0 mg |
| polyvinyl pyrrolidone | 5.0 mg |
| magnesium stearate | 15.0 mg |
| carboxymethyl cellulose | 50.0 mg |
| lactose | 50.0 mg |
| microcrystalline cellulose | 305.0 mg |
| | 500.0 mg |

EXAMPLE 8

Tablets are prepared with the following composition:

| | |
|---|---|
| boric acid | 1.0 mg |
| tartaric acid | 100.0 mg |
| vitamin K$_3$-sodium bisulfite adduct | 10.0 mg |
| polyvinyl pyrrolidone | 5.0 mg |
| magnesium stearate | 15.0 mg |
| lactose | 50.0 mg |
| carboxymethyl cellulose | 50.0 mg |
| microcrystalline cellulose | 269.0 mg |
| | 500.0 mg |

The following in vitro and in vivo tests were performed with the tablets of the invention.

In vitro test

Sperms having been obtained from 32 normo zoospermia persons were examined. From the sperm 1 ml quantities containing 10 to 100 millions of spermiums were mixed with 1 ml suspension obtained from 1 tablet at +38° C. on a watch-glass. The motion of the spermiums was observed. The partial immobilisation began 1 minute after the mixing and became complete in 5 to 10 minutes depending on the vitality of the spermium. The immobilized spermiums became eosin binder which means the cell death. This process is irreversible. The spermiums could not be revived either by changing the pH or by adding fresh serum or by other methods.

In vivo model test

The following test was carried out by women which were in an ovulation period. The tablets prepared according to the invention were wetted by water thereafter inserted into the back-vaginal fornix. After 5 minutes the vagina was exposed and each 2 ml of a sperm having a concentration of 160 to 240 millions spermium/ml were injected onto the women's cervix. The exposing instrument was removed and after 5 and 10 minutes repeated exposures were performed thereafter the content of the vagina was examined.

According to the microscopic examinations the immobilization is 50% after 5 minutes, while 100% after 10 minutes.

In vivo application test

The tablets were applied to women who were capable of conceiving and until the time of the examination protected themselves only by the Ogino-Knaus rule. Among these women pregnancy occurred only in two cases during a one year period. In view of this fact the tablets of the inventions have the same efficiency as the hormonal preparation (the Pearl-index was 2).

The women examined were controlled by gynecologic examination in every two or three months so that the occasional side effect on the vagina or the damaging effect on the mucous membrane should be determined. Such cases were not found. In view of the above it can be stated that the vaginal tablets of the invention are suitable for modern contraception in every respect.

We claim:

1. A contraceptive vaginal tablet comprising 0.2 to 3 parts by weight of boric acid, 10 to 20 parts by weight of tartaric acid, 1 to 2 parts by weight of vitamin $K_3$-sodium bisulfite adduct, 0.8 to 1.2 parts by weight of polyvinyl pyrrolidone, 2 to 5 parts by weight of magnesium stearate, 8 to 12 parts by weight of carboxymethyl cellulose, 8 to 12 parts by weight of lactose and 50 to 65 parts by weight of microscrystalline cellulose.

2. The method comprising applying an effective amount of vitamin $K_3$ sodium bisulfite in composition form to the back vaginal fornix to prevent conception.

* * * * *